United States Patent
Eglmeier et al.

(10) Patent No.: US 9,028,615 B2
(45) Date of Patent: May 12, 2015

(54) DOMESTIC APPLIANCE HAVING A SURFACE WHICH COMPRISES A PHOTOCATALYST

(75) Inventors: Hans Eglmeier, Berlin (DE); Andreas Hanau, Berlin (DE); Hartmut Schaub, Brieselang (DE); Ingo Schulze, Panketal (DE)

(73) Assignee: BSH Bosch und Siemens Hausgeraete GmbH, Munich (DE)

( * ) Notice: Subject to any disclaimer, the term of this patent is extended or adjusted under 35 U.S.C. 154(b) by 746 days.

(21) Appl. No.: 13/320,110

(22) PCT Filed: May 28, 2010

(86) PCT No.: PCT/EP2010/057411
§ 371 (c)(1),
(2), (4) Date: Nov. 11, 2011

(87) PCT Pub. No.: WO2010/139623
PCT Pub. Date: Dec. 9, 2010

(65) Prior Publication Data
US 2012/0055513 A1 Mar. 8, 2012

(30) Foreign Application Priority Data
Jun. 4, 2009 (DE) .......................... 10 2009 026 712

(51) Int. Cl.
| | |
|---|---|
| *B08B 6/00* | (2006.01) |
| *B08B 9/00* | (2006.01) |
| *B08B 9/20* | (2006.01) |
| *B01J 23/00* | (2006.01) |
| *D06F 39/00* | (2006.01) |

(Continued)

(52) U.S. Cl.
CPC ................. *D06F 39/00* (2013.01); *A47L 15/42* (2013.01); *A61L 9/205* (2013.01)

(58) Field of Classification Search
CPC .............. B08B 6/00; B08B 9/00; B08B 9/20; B08B 2209/00; B01J 23/00; B01G 23/047
USPC ....... 134/1, 42, 56 D, 25.2, 57 D, 166 R, 200; 68/12.27, 28; 502/350, 349; 423/610
See application file for complete search history.

(56) References Cited

U.S. PATENT DOCUMENTS

| | | | |
|---|---|---|---|
| 4,955,208 A | 9/1990 | Kawashima et al. | |
| 6,794,065 B1 | 9/2004 | Morikawa et al. | |

(Continued)

FOREIGN PATENT DOCUMENTS

| | | | |
|---|---|---|---|
| CN | 101033317 | * | 9/2007 |
| CN | 101033317 A | | 9/2007 |

(Continued)

OTHER PUBLICATIONS

International Search Report PCT/EP2010/057411.

(Continued)

*Primary Examiner* — Saeed T Chaudhry
(74) *Attorney, Agent, or Firm* — Nixon & Vanderhye, P.C.

(57) ABSTRACT

A domestic appliance includes at least one component having a surface that can become laden with organic dirt. The surface includes a photocatalyst and is made from a primary-formed first material in which the photocatalyst is dispersed. A photoradiation source is provided for irradiating the photocatalyst with an activating electromagnetic radiation.

32 Claims, 3 Drawing Sheets

(51) Int. Cl.
*A47L 15/42* (2006.01)
*A61L 9/20* (2006.01)

(56) References Cited

U.S. PATENT DOCUMENTS

| 7,075,917 | B2 | 7/2006 | Herrmann | |
|---|---|---|---|---|
| 7,524,793 | B2 * | 4/2009 | Orth-Gerber et al. | 502/350 |
| 2002/0116959 | A1 * | 8/2002 | Ohta et al. | 68/12.27 |
| 2007/0131259 | A1 * | 6/2007 | Classen | 134/56 D |
| 2008/0236183 | A1 | 10/2008 | Iimura | |

FOREIGN PATENT DOCUMENTS

| EP | 1602774 | A1 | | 12/2005 |
|---|---|---|---|---|
| JP | 1999-123299 | | * | 5/1999 |
| JP | 11123299 | A | | 5/1999 |
| JP | 11137881 | A | | 5/1999 |
| JP | 11137894 | A | | 5/1999 |
| JP | 1999123299 | A | | 5/1999 |
| JP | 2000245994 | A | | 9/2000 |
| WO | 2008052975 | A2 | | 5/2008 |

OTHER PUBLICATIONS

National Search Report DE 10 2009 026 712.3.
English Translation of Office Action issued in corresponding Chinese Application No. 201080024086.1, mailed Aug. 15, 2013 with English Translation of Search Report (5 pages).

* cited by examiner

DOMESTIC APPLIANCE HAVING A SURFACE WHICH COMPRISES A PHOTOCATALYST

BACKGROUND OF THE INVENTION

The present invention relates to a domestic appliance having at least one component which comprises a surface that can become laden with organic dirt, said surface comprising a photocatalyst and said surface being associated with a photoradiation source for irradiating the photocatalyst with an activating electromagnetic radiation.

A domestic appliance of this type is disclosed by each of the publications JP 11-123299 A, JP 11-137894 A and JP 11-137881 A. Accordingly, a washing solution container and, contained therein, a washing drum rotatable about a vertical axis and coated with layers of a photocatalyst are arranged in a washing machine, and a movable ultraviolet light source is provided by means of which the layers can be irradiated with ultraviolet light to activate the photocatalyst. Parts of the washing drum that could shade a layer of the photocatalyst from the photoradiation source can be made from material which is transparent to the radiation.

In a water-carrying domestic appliance, in general, objects that are soiled with different types of dirt are cleaned. Thus, in a dishwasher, food residues arise and the range of soiling of laundry items to be cleaned in a washing machine is usually greater. It is common to all water-carrying domestic appliances that soiling occurs therein, particularly at the less accessible sites, and can accumulate at such sites. Such soiling can be a good nutrient medium for microorganisms such as bacteria and fungi in a moist warm atmosphere prevailing in such a domestic appliance and can thereby cause additional soiling.

For example, in a laundry treatment device such as a washing machine, on frequent use of wash programs with cold washing solutions, in a long phase of inactivity with the door closed or under unfavorable siting conditions, bad odors and/or visible soiling can occur. A possibility for cleaning at such poorly accessible regions is therefore desirable. It is also desirable that preventative measures can be taken against microorganisms even where no externally perceptible effects occur. Overall, therefore, it is useful if such nuisance soiling can be prevented or, as far as possible, eliminated.

A variety of measures against such soiling are known from the prior art. In particular, sometimes, device cleaning programs are offered with which, at high temperatures and with the aid of washing agents and possibly with increased washing solution levels and/or at higher drum rotation speeds, i.e. with an increased input of mechanical energy, built-up dirt can be combated. Also known are the use of ozone and UV-C radiation to remove organic dirt. Also known are measures for killing microorganisms using $Ag^+$ or $Cu^+$ ions in a washing solution or on the surfaces of the materials in contact with the washing solution. Other methods aim at the thermal destruction of any microorganisms present by increasing the temperature at the surfaces of the components in contact with the washing solution by means of direct or indirect energy transfer (water, steam, microwaves). Also known from the aforementioned documents is the use of photocatalysts. A disadvantage of said known methods and measures is, for example, the high cost for equipment and/or operation thereof in order to achieve relevant effects. In the case of the use of $Ag^+$ and $Cu^+$ ions, disadvantageous effects involve the pollution of ground and waterways.

From the documents WO 2005/108505 A1, EP 1 205 244 A1 and EP 1 204 245 A1, minerals are known, the surfaces of which are able to activate oxygen molecules by irradiating them with visible or ultraviolet light such that the readiness thereof to undergo chemical reactions is significantly increased. This effect is commonly known by the designation "photocatalysis". Each of said minerals is a semiconductor with a band gap which permits the creation of an electron-hole pair in said semiconductor by a quantum of visible or ultraviolet light. It is also to be assumed that a mineral of this type has an affinity for oxygen, which permits activation of the oxygen by transferring energy from the semiconductor. The known minerals include titanium dioxide, cadmium sulfide, tungsten trioxide and zinc oxide.

It is also known to alter a semiconductor of this type by doping or similar modification with elements such as carbon, boron, nitrogen, phosphorus, sulfur, chlorine, arsenic, selenium, bromine, antimony, tellurium and iodine such that the wavelength of light needed to evoke the photocatalysis is increased. Titanium dioxide is cited as an example: in order to evoke the photocatalysis with pure titanium dioxide, irradiation with ultraviolet light having a wavelength of between 380 nm and 400 nm corresponding to the UV-A range is required. According to the publication WO 2005/108505 A1, it is possible to generate a titanium dioxide modified with carbon and having the form of a powder at which photocatalysis occurs merely on irradiation with visible light. This powdered photocatalyst is usable in components made from concrete, ceramics, paper and woven fabrics in the building industry and the automotive industry, as well as in photovoltaic cells, air-conditioning units and apparatus for cleaning or sterilizing air or water.

Of the known materials which exhibit photocatalysis under corresponding conditions, titanium dioxide is particularly distinguished by being chemically largely inert and non-toxic, as well as being known in many uses, particularly as a white pigment and being produced and marketed on a large industrial scale.

BRIEF SUMMARY OF THE INVENTION

It is therefore an object of the present invention to provide a domestic appliance of the aforementioned generic type in which or with which, in simple and particularly hygienic means, soiling can be eliminated or prevented or at least largely cleared or prevented. In particular, soiling by microorganisms is to be eliminated or prevented.

This aim is achieved, according to the invention, by the domestic appliance having the features of the relevant independent claim. Preferred embodiments of the domestic appliance according to the invention are disclosed in corresponding dependent claims. Preferred embodiments of the domestic appliance relate to preferred embodiments of the method and vice versa, even if not explicitly indicated herein.

The subject matter of the invention is therefore a domestic appliance comprising at least one component which has a surface that can become laden with organic dirt, said surface having a photocatalyst and being associated with a photoradiation source for irradiating the photocatalyst with an activating electromagnetic radiation, the surface being made from a primary formed first material in which the photocatalyst is dispersed.

In the domestic appliance according to the invention, essentially any internal surfaces can comprise a photocatalyst.

In visually relatively inaccessible regions of a domestic appliance according to the invention (e.g. the region of the washing solution container behind the rear wall of the drum in a corresponding washing machine), even illumination can be achieved with additionally arranged photoradiation sources or suitably configured devices for optical deflection of the electromagnetic radiation using mirror surfaces (e.g. the rear wall of the inner drum). Given a suitable configuration of the inner surfaces of the domestic appliance with the photocatalyst, particularly effective cleaning can thus be achieved.

In a preferred embodiment of the domestic appliance according to the invention, the photocatalyst is a filler in the first material; more preferably, the first material is a first polymer material filled with the filler and, particularly preferably, the first material is a thermoplastics material filled with the filler. In particular, the first material can be processed by injection molding. In this case, the thermoplastics material forms a continuous matrix in which the filler is dispersed. Insofar as the filler is present at the surface, said filler is accessible to irradiation by the photoradiation source with simultaneous exposure to oxygen and the catalytic effect thereof can take effect, so as to contribute to the generation of activated oxygen, which is suitable for removing undesirable deposits and for disinfection by oxidation.

In a further preferred embodiment of the domestic appliance according to the invention, the first material is provided as a layer on the surface and covers a second material. In the first material, the filler which is usable, according to the invention, as a photocatalyst is, in any event, not catalytically active remotely from the surface; it is therefore conceivable to use a second material remote from the surface which, in particular, can comprise a different filler and can also be the same as or similar to the first material. A suitable component can be produced, for example, by a two-stage injection molding process, wherein firstly the first material and then the second material is molded, so that the first material forms the surface and the second material then completely fills the mold used for injection molding. In the second material, in particular, a filler that is cheaper than the photocatalyst, such as talcum, can be present. The second material can have similar or different mechanical properties compared with the first material.

In a particularly preferred embodiment of the domestic appliance according to the invention, the photocatalyst is a semiconductor mineral, particularly titanium dioxide, cadmium sulfide, tungsten trioxide or zinc oxide. This mineral can be modified, in particular, to enable photocatalysis on irradiation with visible light through the addition of carbon, boron, nitrogen, phosphorus, sulfur, chlorine, arsenic, selenium, bromine, antimony, tellurium or iodine.

Especially preferable in the context of the invention is the use of titanium dioxide as a filler. Titanium dioxide occurs in different forms. For the present invention, it has proved to be particularly advantageous if titanium dioxide is present in the anatase form. However, this is not to exclude other forms of titanium dioxide, specifically rutile and brookite, for use in the context of the invention. Also especially preferable is a titanium dioxide which is modified by doping with carbon. It should be noted that by means of such a modification, a possible disadvantage of the rutile or brookite forms of titanium dioxide can be balanced out.

The mineral forming the photocatalyst lies in the surface, preferably in the form of nanoparticles. Particularly advantageously, the mineral consists of particles having a mean diameter d of less than or equal to 10 nm, particularly particles having a mean diameter d of less than or equal to 8 nm.

In a preferred embodiment, the domestic appliance according to the invention comprises a photoradiation source configured to emit the electromagnetic radiation in a wavelength range covering visible light and ultraviolet light.

In particular, the photoradiation source is configured to emit the electromagnetic radiation in the wavelength range from 380 nm to 400 nm.

In a preferred embodiment of the domestic appliance according to the invention, the photoradiation source is an arrangement with at least one light-emitting diode. In a particularly preferred embodiment, the domestic appliance has an arrangement of this type with at least six light-emitting diodes which emit electromagnetic radiation in the range from 380 nm to 400 nm.

According to the invention, any number of light-emitting diodes can be used, said light-emitting diodes particularly emitting electromagnetic radiation in the range from 380 nm to 400 nm and, preferably, in the range from 385 nm to 395 nm in order to evoke the desired effect with the photocatalyst used. For this purpose, it is also necessary that the wavelength of a maximum in an intensity distribution of a light-emitting diode of this type lies within this wavelength range. Merely portions of electromagnetic radiation in the respective desirable wavelength range are sufficient, although diodes with a large radiation portion in said region are preferably used. Light-emitting diodes that are suitable for emitting UV radiation are based on semiconductors such as gallium nitride, indium gallium nitride, zinc selenide and silicon carbide. Such light-emitting diodes and arrays thereof, that is, readymade arrangements of such light-emitting diodes produced as constructional units are commercially available.

The domestic appliance according to the invention is fundamentally unrestricted with regard to the intended use thereof. For example, therefore, refrigerators, stoves, microwave ovens, etc. come into consideration. Preferably, the domestic appliance is a water-carrying appliance, in particular a dishwasher or a laundry treatment device. The domestic appliance is particularly preferably a laundry treatment device belonging to the group washing machine, laundry drier and washer-drier. In general, a laundry treatment device comprises a rotatably mounted drum, a drive motor for the drum and a heating device. In addition, as a rule, switching means and drive means for rotating and stopping the drum are provided.

A laundry drier generally comprises a compressed air channel in which a drying chamber for the items to be dried and, in general, a heater for heating the drying air and a blower for conveying the drying air are situated. A laundry drier is generally operated as a circulating air laundry drier or an extracted air laundry drier, although mixed forms are also known. In a circulating air laundry drier, for the drying of goods such as laundry, drying air is fed in a closed circuit through a drying chamber with the goods to be dried. Moist warm air flowing out of the drying chamber is cooled in order to condense out the moisture originating from the damp goods in a suitable heat exchanger (air-to-air heat-exchanger, or heat sink of a heat pump) and, following separation of the condensate produced, heated again and fed back into the drying chamber. In an extracted air laundry drier, however, an air feed channel and an extracted air channel are provided so that the drying air drawn from the surroundings of the extracted air drier (particularly an installation room) into the air feed channel is fed, after passing through the drying chamber, via the extracted air channel to an extracted air outlet and then back into the installation room or through a suitable exhaust air conduit out of the room.

A washing machine generally comprises, apart from a drum as the receptacle container for the laundry items to be treated, a washing solution container, a water feed system and a washing solution outlet system with a washing solution pump arranged on the base of the washing solution container.

A washer-drier unites the features of a laundry drier and a washing machine and is usable for both uses.

If the domestic appliance according to the invention is a laundry treatment device, said device has, in particular, laundry agitators, a seal, a washing solution container and/or another component which is exposed to the laundry items to be treated and is, particularly, primary-formed as a whole, having a surface which contains the photocatalyst.

In a preferred embodiment of the water-carrying domestic appliance according to the invention, comprising at least one primary-formed component which can be exposed to a washing solution, said component comprises the surface in which the photocatalyst is dispersed. By this means, the component is accessible to cleaning with activated oxygen via the agency of the photocatalyst provided according to the invention. The component is also preferably selected from the group comprising seal, laundry agitator and washing solution container.

Where the photocatalyst is present on a laundry agitator or another component of a washing machine, laundry drier or washer-drier directly exposed to the laundry items, odor-correcting or bleaching effects on the laundry items moving in the inner drum can be useful. This can be achieved in that, on contact with the titanium dioxide-coated surfaces, where immediately beforehand or simultaneously the photocatalysis is activated in the direct vicinity of the contact surface, activated oxygen generated acts on the adjacent non-treated surfaces equally.

In another preferred embodiment of the domestic appliance according to the invention, the photoradiation source is arranged in the vicinity of an access opening, which can be, for example, a door of a corresponding washing machine. The photoradiation source can advantageously be an illumination device which illuminates a working area of the domestic appliance, for example, the interior of the washing drum of a washing machine and allows a user to examine the interior of the operating domestic appliance. The photoradiation source combines the use for activation of the photocatalyst with use for displaying the operational state of the domestic appliance and use for illuminating an operational region used by a user who wishes to gain a view of the interior. The invention is therefore suitable, in particular, for use with domestic appliances which already comprise electric illumination devices in the interior thereof. The photoradiation source provided according to the invention can preferably be used in combination with, in place of, or alternating with an existing internal space illumination. However, said source can also be used at any other suitable sites in the interior and/or poorly ventilated regions of a domestic appliance.

In embodiments wherein further photoradiation sources are present in the domestic appliance, said sources possibly emitting radiation in the visible portion of the spectrum, said sources can possibly also be used for activating the photocatalyst. A variety of light effects can possibly be generated. For example, at the start of a cleaning process according to the invention, a special illumination program with changing colors can be started, in order to indicate that the cleaning is being carried out.

Alternatively or additionally, particular sounds or tones can be generated, in order to indicate that the cleaning is being carried out.

In a preferred embodiment of the invention, a UV-A light-emitting diode or a UV-A light-emitting diode array is used in the region of a drum internal illumination of a washing machine. The regions in the washing solution container and the door seal of the washing machine thereby irradiated comprise a layer containing titanium dioxide. The generation of the titanium dioxide-containing layer takes place, generally, during the manufacturing process for the component. The polypropylene usually reinforced with talcum or glass fiber which is used for washing solution containers made from plastics can also or alternatively be enriched with titanium dioxide in an injection molding process so that a titanium dioxide-containing layer is formed on an inner surface of the washing solution container. In similar manner, this can be accomplished with an EPDM door seal during the vulcanization process.

In a particularly preferred embodiment of the invention, the domestic appliance has an optical sensor with a light source and a light sensor, wherein the light source is the photoradiation source. Thus, the photoradiation source fulfils a plurality of functions in this embodiment also. It is naturally necessary that the photocatalyst is present in the vicinity of the sensor and can be reached by the radiation emitted by the photoradiation source.

In another particularly preferred embodiment, the domestic appliance according to the invention has an odor sensor. An odor sensor of this type can be arranged at a variety of sites. In a domestic appliance configured as a laundry drier, the odor sensor is preferably arranged in the drying chamber and/or in the drying air channel behind the drying chamber. If the laundry drier is a condensation drier, it is suitable, for example, to arrange the odor sensor behind a heat exchanger in which the moisture of the warm moist drying air can condense. By this means, the influence of the moisture on the sensor signal of the odor sensor can be minimized. In a domestic appliance according to the invention configured as a washing machine, the odor sensor is preferably arranged in the drum. This arrangement enables registration of odor substances before performing a washing process, so that cleaning can be performed before the start of washing. Where used in a washing machine, the odor sensor can be protected, before the introduction of water or washing solution, against water or washing solution possibly by means of a closable cover.

It is also an object of the invention to provide a method for cleaning a surface of at least one component of a domestic appliance that can become laden with organic dirt, said surface having a photocatalyst dispersed therein and being associated with a photoradiation source for irradiating the photocatalyst with an activating electromagnetic radiation, and wherein the surface is made from a primary-formed first material, said method involving the photocatalyst being activated by the photoradiation source by irradiation with electromagnetic radiation.

In embodiments of the method according to the invention, the cleaning can be started manually or automatically. Automatic starting can be carried out in, for example, a laundry treatment program before the start, during or after ending of the laundry treatment program.

Alternatively, the start of a cleaning process according to the invention can be linked to the recognition of soiling and/or bad odors. Thus, in one embodiment of the invention, an odor sensor is present in the domestic appliance. After detection by the odor sensor of a bad odor, the method according to the invention can be started, the time point for the start of the method being variably selectable. The cleaning process can be carried out at once and, in principle, before, during or after performance of the laundry handling program. In order to recognize bad odors, suitable reference signals can be stored in a program control system of the domestic appliance. According to the invention, it is preferable that, on detection of a pre-defined odor-causing substance or a pre-defined odor-causing substance mixture or on overshooting a particular threshold value for the concentration of a pre-defined odor-causing substance or a pre-defined odor-causing substance mixture, a method according to the invention for cleaning a domestic appliance is carried out.

The duration of the method according to the invention can differ according to the individual case and can be linked to the fulfillment of various preconditions. For instance, the time and duration of the method according to the invention may depend on a period elapsed since the performance of a last cleaning process or laundry treatment program. For this purpose, a suitable clock can be present in a program control system of the domestic appliance.

In a preferred embodiment of the method according to the invention, the carrying out of the cleaning process according to the invention is indicated by means of an acoustic and/or optical signal. According to the invention, it is therefore preferable that the presence of an odor-causing substance is indicated by means of an indicating device of the domestic appliance. Said indicating can be carried out by means of an acoustic and/or optical indicating device.

The invention has the advantage that, by simple and economical means, a domestic appliance is provided together with associated means for the cleaning thereof and which tends significantly less to soiling, particularly with microorganisms, and which is easy to clean should soiling nevertheless occur.

The domestic appliance according to the invention and the method according to the invention which can be carried out therein have the advantage that cleaning can be carried out in a simple and automatic manner. Said cleaning can be carried out automatically, for example, before performing or after completion of a laundry treatment program or following detection of soiling (e.g. odor-causing substances). In this way, laundry treatment programs and cleaning programs can be adjusted to the type and quantity of organic compounds and particularly microorganisms that may be present.

BRIEF DESCRIPTION OF THE DRAWINGS

Further details of the invention are disclosed in the following description of non-restricting exemplary embodiments of the domestic appliance according to the invention and of the method according to the invention for cleaning a domestic appliance. Reference will be made to FIGS. 1 and 2 in which a laundry treatment device is illustrated as the domestic appliance. Other embodiments are also conceivable. In the drawings.

DETAILED DESCRITION OF EXEMPLARY EMBODIMENTS OF THE PRESENT INVENTION

Figure 1:
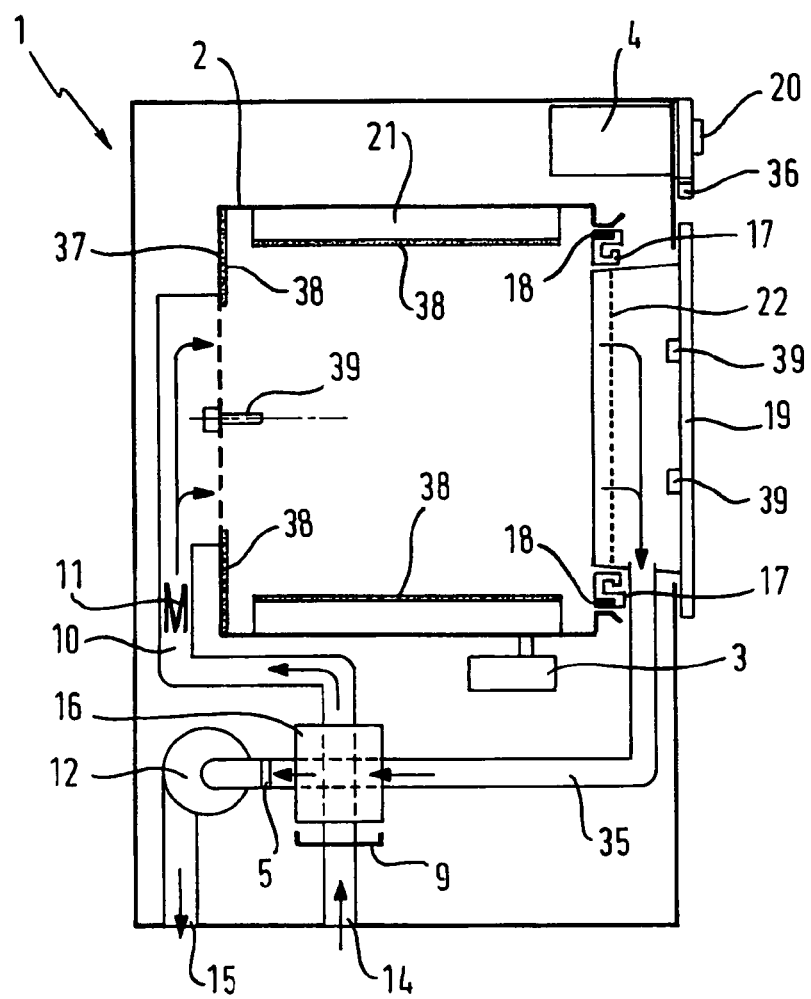
FIG. 1 is a vertical section through a first embodiment of a domestic appliance configured as an extracted air laundry drier.

The extracted air laundry drier 1 shown in FIG. 1 comprises a drum 2 rotatable about a horizontal axis as the drying chamber within which agitators 21 are fastened for moving laundry items during a drum rotation. Said agitators 21 are primary-formed, specifically injection molded, from a thermoplastics polymer which comprises titanium dioxide in the anatase form as the filler (with regard to the photocatalyst and the polymer, see reference signs 43 and 44 in FIG. 3, which is described below). The titanium dioxide is made in powdered form and bound to the polymer. Said titanium dioxide can be doped with carbon in order to be activatable by visible light as a photocatalyst. It should be noted that the use of titanium dioxide as a filler is entirely common practice, although said filler is sometimes chemically deactivated in order to prevent the photocatalytic effect, which may be entirely undesirable in uses different from those herein. In the present case, care must therefore be taken that deactivated titanium dioxide of the latter type is not used.

In order to operate the extracted air laundry drier 1, drying air is fed, by the aid of the blower 12 from an air feed inlet 14 in an air feed channel 10 via a heater 11 through the drum 2 containing the laundry items to be dried and an extracted air channel 35 to an extracted air outlet 15. In said extracted air laundry drier, therefore, the air feed channel 10, the drum 2 and the extracted air channel 35 form a drying air channel. Air warmed by the heater 11 is fed through the perforated surface of the drum rear wall 37 into the drum 2, comes into contact there with the laundry items to be dried and flows through the filling opening of the drum 2 to a lint sieve 22 within the door 19 which closes the filling opening. The moist warm drying air is then deflected downward in the door 19. The drying air is fed in the extracted air channel 35 to an air-to-air heat exchanger 16 in which the hot drying air laden with moisture is cooled and is subsequently fed to an extracted air outlet 15. The condensed moisture is collected in a condensation collecting container 9 and can be removed therefrom, for example, by pumping with a condensation pump (not shown).

For cooling the drying air laden with moisture extracted from the laundry items, in the air-to-air heat exchanger 16, ambient air fed via the air feed channel 10 to the drier 1 is used. This air drawn in is warmed by the warm drying air laden with moisture and further heated before entry into the drum 2 by means of the heater 11.

In the embodiment shown in FIG. 1, the drum 2 is mounted at the rear base by means of a rotary bearing and at the front by means of an endshield 17, the drum 2 lying with a brim on a sliding strip 18 on the end shield 17 and being thereby held at the front end. A motor 3 drives the drum 2. The extracted air drier 1 is controlled by means of a program control system 4 which can be controlled by a user via an operating unit 20. 36 identifies an indicating means for output of information concerning a possibly occurring cleaning process according to the invention. If a bad odor is identified by means of an odor sensor (not shown, but see reference character 5 in FIG. 2), for example a light-emitting diode 39 which outputs electromagnetic radiation in the wavelength range from 380 nm to 400 nm can be switched on. Said electromagnetic radiation (e.g. UV-B radiation) causes oxygen radicals to be generated at the layer containing activated titanium dioxide which acts as the photocatalyst, said oxygen radicals being able to break down soiling.

In the embodiment shown in FIG. 1, light-emitting diodes 39 which form the photoradiation source 39 required for activation of the photocatalyst are arranged at the door 19 and at the drum rear wall 37.

Figure 2:
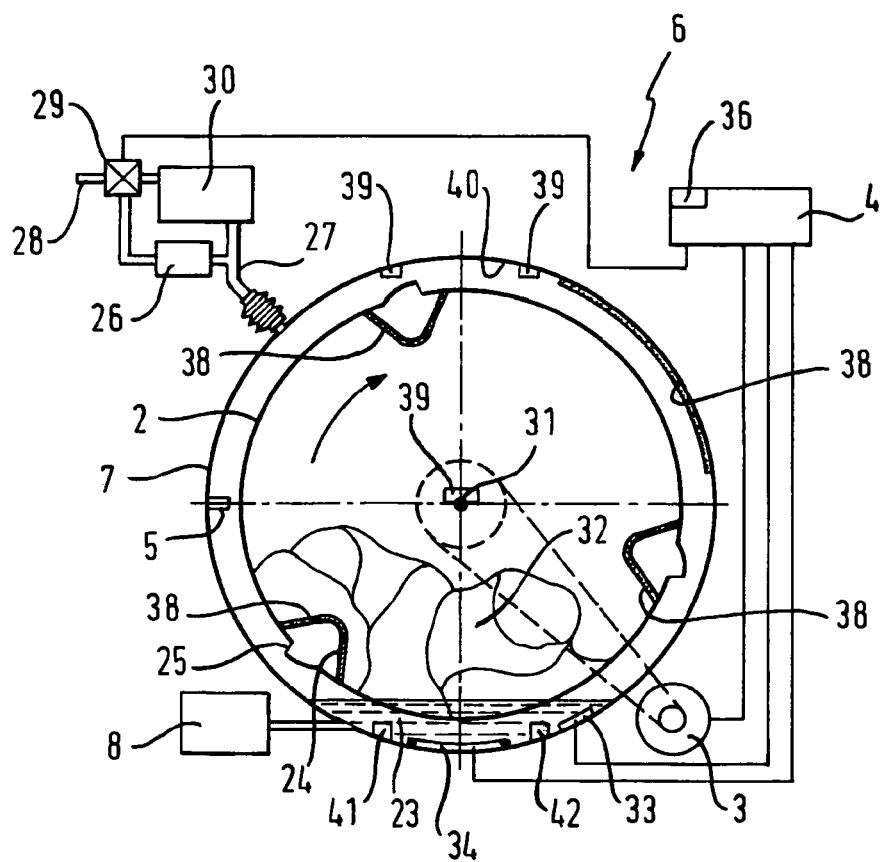
FIG. 2 is a schematic representation of a vertical section through a second embodiment of the domestic appliance configured as a washing machine.

FIG. 2 is, in particular, a schematic drawing of the parts of a washing machine 6 that are relevant to the present invention, in which a corresponding method can be carried out. The washing machine 6 has a washing solution container 7 in which a drum 2 is rotatably mounted and drivable by a motor 3. The rotary axis 31 of the drum 2 is oriented by a small angle (e.g. 13°) upward out of the horizontal toward the front, so as to provide easier access to and viewing of the interior of the drum 2. With this arrangement, in conjunction with specially configured laundry agitators 24 and scoop devices 25 for the washing solution 23 at the inner surface of the drum jacket, intensification of the drenching of the laundry items 32 with washing solution is also achieved.

The primary-formed laundry agitators 24 and an inner wall 40 of the also primary-formed washing solution container 7 have surfaces 38 which again comprise titanium dioxide in the anatase form. In order to generate oxygen radicals at these layers 38, light-emitting diodes 39 which emit electromagnetic radiation in the wavelength range from 380 nm to 400 nm are also arranged at the inner wall 40 of the washing solution container 7 and in the drum 2.

The washing machine 6 also has a washing solution feed system comprising a water connection fitting for the domestic water supply 28, an electrically controlled valve 29 and a feed pipe 27 to the washing solution container 7, said feed pipe being directed via a dispenser drawer 30 from which the feed water can transport washing agent portions to the washing solution container 7. A dosing device 26 enables, in cooperation with the domestic water supply 28, the feeding of fabric softener into the washing solution container 7. A heating device 34 is also arranged in the washing solution container 7. The valve 29 and the heating device 34 can be controlled by a control device (program control system) 4 depending on a program sequence plan, which can be linked to a time program and/or to the achievement of certain measured values of parameters such as washing solution level, washing solution temperature, rotary speed of the drum 2, etc. within the washing machine 6. 33 denotes a sensor for measuring the hydrostatic pressure p in the washing solution container 7. 8 denotes a pump for the liquid situated in the washing solution container 7.

In the embodiment shown in FIG. 2, an odor sensor 5 is arranged within the washing solution container 7. 36 denotes an indicator means for output of the information concerning a cleaning process that might be taking place or is due.

Finally, the domestic appliance in the embodiment of FIG. 2 has an optical sensor 41, 42 with a light source 41 and a light sensor 42, the light source 41 comprising a light-emitting diode 41 which emits electromagnetic radiation in the wavelength range from 380 nm to 400 nm. The surroundings of the light sensor 42 also have titanium dioxide as a photocatalyst in the surfaces 38 of primary-formed components such as the washing solution container 7. The light-emitting diode 41 emits electromagnetic radiation in the wavelength range from 380 nm to 400 nm so as to be able to irradiate the titanium dioxide-containing surface 38 for the purpose of activating the photocatalyst.

Figure 3:
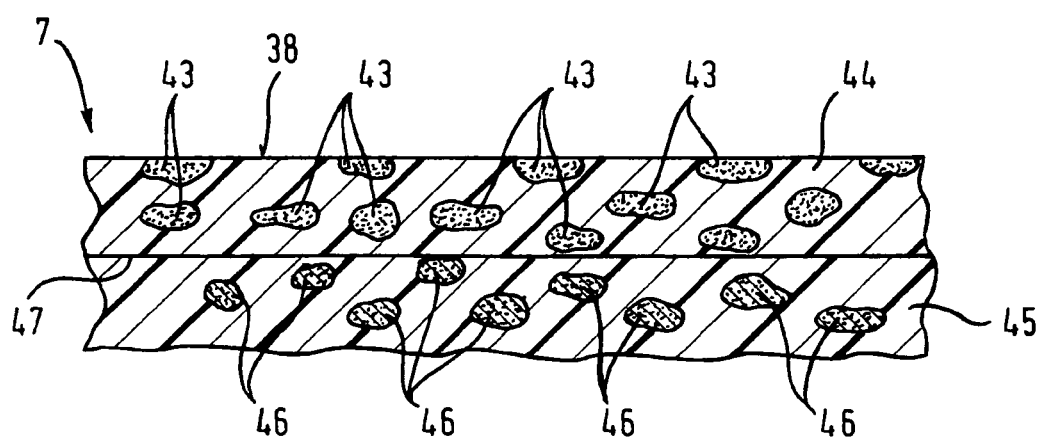
FIG. 3 is a section through a primary-formed component.

FIG. 3 shows a section through a primary-formed, specifically injection molded, component 7 in the form of the washing solution container 7 of FIG. 2, in order to illustrate clearly the surface 38 which contains the photocatalyst 43. The photocatalyst 43 consists of a filler 43 in a first material 44, the first material 44 being a first polymer material 44 filled with the filler 43. The polymer, particularly a thermoplastics material 44 processed by injection molding or alternatively press molding, forms a continuous matrix in which the filler 43 is dispersed.

The first material 44 forms a layer on the surface 38 and covers a second material 45. In the present case, said second material is a thermoplastics polymer filled with another filler 46 which can be identical to the polymer of the first material, or at least similar, so as to be capable of processing in the same injection molding tool as the first material 44. In this way, the component 7 can be generated in a two-stage injection molding process, the first material 44 being initially injected into a given mold and only partially filling said mold, whereupon subsequently and before complete solidification of the first material 44, the second material 45 is injected until the mold is entirely filled, and said second material 45 comes to lie under the first material 44 which forms a layer on the surface 38. The form of the separating surface 47 between the first material 44 and the second material 45 is relatively unimportant, particularly since the photocatalyst 38 can only be catalytically active when lying directly on the surface 38 and thus exposed both to oxygen and activating electromagnetic radiation. For this reason, the filler 46 in the second material 45 does not also need to be photocatalytically active; the filler 46 can be talcum or the like, according to normal practice and it is also conceivable for glass fibers to be used in order to impart a higher degree of strength or other favorable properties to the second material 45 than to the first material 44. It may also only be desired to use a more economical material than titanium dioxide in the second material 45.

In any case, a semiconductor mineral 43 is used as the photocatalyst 43, specifically in the present case, a mineral 43 made essentially from titanium dioxide 43, in that the titanium dioxide 43 is present in the anatase form and also has a doping of carbon. Thus, visible light can be used to activate the photocatalyst, which enables the use of less expensive photoradiation sources 39, 41 than light-emitting diodes which emit UV light. The mineral 43 is present in the form of particles 43 with a mean diameter d smaller than or equal to 10 nm in the first material 44.

The invention claimed is:

1. A domestic appliance, comprising:
   at least one component having a surface that is prone to accumulate organic dirt as a result of use of the appliance, said surface comprising a photocatalyst and being made from a primary-formed first material in which the photocatalyst is dispersed; and
   a photoradiation source for irradiating the photocatalyst with an activating electromagnetic radiation.

2. The domestic appliance of claim 1, wherein the photocatalyst is a filler in the first material.

3. The domestic appliance of claim 1, wherein the first material is a first polymer material filled with the filler.

4. The domestic appliance of claim 1, wherein the first material is a thermoplastics material filled with the filler.

5. The domestic appliance of claim 1, wherein the first material is provided as a layer on the surface and covers a second material.

6. The domestic appliance of claim 1, wherein the photocatalyst is a semiconductor mineral.

7. The domestic appliance of claim 6, wherein the mineral comprises particles having a mean diameter d of less than or equal to 10 nm.

8. The domestic appliance of claim 1, wherein the photocatalyst is a mineral essentially made of titanium dioxide.

9. The domestic appliance of claim 8, wherein the titanium dioxide is provided in an anatase form.

10. The domestic appliance of claim 8, wherein the titanium dioxide has a doping of carbon.

11. The domestic appliance of claim 1, wherein the photoradiation source is configured to emit the electromagnetic radiation in a wavelength range covering visible light and ultraviolet light.

12. The domestic appliance of claim 11, wherein the photoradiation source is configured to emit the electromagnetic radiation in the wavelength range from 380 nm to 400 nm.

13. The domestic appliance of claim 1, wherein the photoradiation source is an arrangement with at least one light-emitting diode.

14. The domestic appliance of claim 13, wherein the arrangement comprises at least six light-emitting diodes.

15. The domestic appliance of claim 1, constructed in the form of a dishwasher or a laundry treatment device.

16. The domestic appliance of claim 15, further comprising at least one component which can be exposed to a washing solution, said component comprising the surface in which the photocatalyst is dispersed.

17. The domestic appliance of claim 16, wherein the component is a member selected from the group consisting of laundry agitator and washing solution container.

18. The domestic appliance of claim 15, wherein the photoradiation source is arranged in a vicinity of an access opening of the dishwasher or a laundry treatment device.

19. The domestic appliance of claim 1, constructed in the form of a laundry treatment device belonging to a member selected from the group consisting of washing machine, laundry drier and washer-drier.

20. The domestic appliance of claim 1, wherein the photoradiation source is a light source of an optical sensor having a light sensor.

21. The domestic appliance of claim 1, further comprising an odor sensor.

22. The domestic appliance of claim 1, wherein the first material is a thermoplastics material.

23. The domestic appliance of claim 1, wherein the photoradiation source comprises multiple discrete sources.

24. The domestic appliance of claim 1, wherein irradiating the photocatalyst with an activating electromagnetic radiation results in the creation of activated oxygen.

25. The domestic appliance of claim 1, wherein the component comes into physical contact with items placed into the domestic appliance to be cleaned.

26. The domestic appliance of claim 1, wherein the component supports a second component which comes into physical contact with items placed into the domestic appliance to be cleaned.

27. The domestic appliance of claim 1, wherein the component comes into contact with organic dirt during or as a result of a wash cycle.

28. The domestic appliance of claim 1, wherein the domestic appliance is a washing machine.

29. The domestic appliance of claim 1, wherein the component is an inaccessible component, the inaccessible component being a portion of the domestic appliance which is not visible to a user while loading or unloading the appliance.

30. The domestic appliance of claim 1, wherein the surface of the component is located in a section of the appliance which is in contact with stagnant air when not in an active cycle.

31. The domestic appliance of claim 29, wherein the component is a washing machine.

32. A method, comprising:
    making a surface of at least one component of a domestic appliance from a primary-formed first material;
    dispersing in the surface a photocatalyst; and
    activating the photocatalyst by a photoradiation source through irradiation with electromagnetic radiation for cleaning the surface that can become laden with organic dirt.

* * * * *